United States Patent [19]
Slatkine

[11] Patent Number: 5,836,938
[45] Date of Patent: Nov. 17, 1998

[54] HAIR REMOVAL WITH A LASER SYSTEM AND WAVEGUIDE FOR RADIAL TRANSMISSION OF LASER ENERGY

[76] Inventor: Michael Slatkine, 59 Brenner Street, Herzlia, Israel, 46427

[21] Appl. No.: 769,492

[22] Filed: Dec. 18, 1996

[51] Int. Cl.⁶ .................................................. A61B 17/36
[52] U.S. Cl. .................................. 606/9; 606/13; 606/16
[58] Field of Search ................... 606/2, 3, 7, 9, 606/10, 13–17; 607/88, 89

[56] References Cited

U.S. PATENT DOCUMENTS

| | | | |
|---|---|---|---|
| 3,693,623 | 9/1972 | Harte et al. .................................. | 606/9 |
| 3,834,391 | 9/1974 | Block .......................................... | 606/9 |
| 4,216,775 | 8/1980 | Cottingham ................................ | 606/36 |
| 4,617,926 | 10/1986 | Sutton ......................................... | 606/9 |
| 4,693,244 | 9/1987 | Daikuzono . | |
| 4,736,743 | 4/1988 | Daikuzono . | |
| 4,940,466 | 7/1990 | Paduano et al. ........................... | 606/36 |
| 5,046,810 | 9/1991 | Steiner et al. . | |
| 5,129,897 | 7/1992 | Daikuzono . | |
| 5,133,709 | 7/1992 | Prince . | |
| 5,139,495 | 8/1992 | Daikuzono . | |
| 5,190,535 | 3/1993 | Daikuzono . | |
| 5,194,712 | 3/1993 | Jones . | |
| 5,250,068 | 10/1993 | Ideguchi et al. . | |
| 5,269,777 | 12/1993 | Doiron et al. . | |
| 5,647,866 | 7/1997 | Zaias et al. ................................. | 606/9 |

FOREIGN PATENT DOCUMENTS

| | | |
|---|---|---|
| 0 292 621 A1 | 11/1988 | European Pat. Off. . |
| 0514258 | 5/1992 | European Pat. Off. . |
| 2209577 | 3/1992 | Japan . |
| 2209578 | 3/1992 | Japan . |
| 214739 | 2/1985 | United Kingdom ..................... 606/36 |
| 2214084 | 8/1989 | United Kingdom . |
| WO 92/17243 | 10/1992 | WIPO . |

OTHER PUBLICATIONS

"Light scattering properties of a rough–ended optical fibre", H. Fujii, et al., Optica and Laser technology, Feb. 1984.

*Primary Examiner*—Robert L. Nasser
*Attorney, Agent, or Firm*—Cobrin Gittes & Samuel

[57] ABSTRACT

Apparatus and method of hair depilation for destroying follicle cells is provided where an invasive element, such as a waveguide, probe or needle, is inserted into a hair follicle and pulsed laser energy is radially transmitted through the invasive element to the entire lining of the follicle. The blood vessels of the papilla, the hair shaft, the hair bulge and hair bulb are substantially damaged. The laser employed may be at a wavelength that does not penetrate skin. The laser may pulse laser energy through a frosted tip of a waveguide or probe that scatters the laser radiation radially along a length of the frosted tip to the follicle lining. Otherwise, a protective substances, such as energy absorbing particles, may be used to absorb energy and transmit it to the follicle lining such that there is no damage to the outlying skin. Alternatively, a waveguide may be placed in a needle and the needle inserted into a hair follicle. The energy provided by the waveguide is conducted by the needle and radially transmitted to the follicle lining. By the use of a needle, either a frosted fiber or a flat fiber which provides laser energy forward from its tip in a conical shape may be used.

17 Claims, 2 Drawing Sheets

HAIR REMOVAL WITH A LASER SYSTEM AND WAVEGUIDE FOR RADIAL TRANSMISSION OF LASER ENERGY

BACKGROUND OF THE INVENTION

The present invention relates to a method of hair removal with a laser light source and an optical waveguide.

Hair depilation techniques utilizing optical fibers are known. U.S. Pat. No. 3,693,623 discloses the use of a flat fiber that is inserted into a follicle and whose end is aimed at the papilla. Laser energy that passes through the fiber emerges from the end of the fiber in the shape of a cone whose axis of symmetry coincides with the longitudinal axis of the fiber. This technique assures only papilla destruction instead of all cells that contribute to new hair growth, such as the bulge cells. Also, because of the high power density used with this method, non-follicle tissue below the papilla is damaged.

U.S. Pat. No. 3,538,919, which also discloses a fiber optic that disperses laser energy and targets the papilla. This fiber optic is covered with a catheter jacket to prevent laser energy from leaking through the sides.

Another method of hair depilation involves applying laser radiation to the skin having light skin color, whereupon the laser radiation disperses throughout the tissue. Radiation within the proximity of a follicle is absorbed by the follicle so that only a small percentage of the applied laser energy destroys the follicle lining.

SUMMARY OF THE INVENTION

A method of hair depilation for destroying follicle cells is provided where an invasive element is inserted into a hair follicle and pulsed laser energy is radially transmitted along a length of invasive element to irradiate substantially the entire lining of the follicle. The blood vessels of the papilla, the hair shaft, the hair bulge and hair bulb are destroyed from the laser radiation.

Where a laser is employed at a wavelength that does not penetrate skin, e.g., a holmium laser at 2.1 $\mu$ wavelength, the invasive element is a waveguide or probe, preferably having an elongated frosted tip that contains roughened fiber that scatters the laser radiation radially along a length of the frosted tip. The length of the frosted tip is preferably less than a depth of the hair follicle so as to avoid damaging the external surface of the skin at the entrance to the hair follicle. Where a laser is employed at a wavelength which does penetrate the skin, a protective substance is used to block deep penetration of the laser radiation that may otherwise damage the outlying skin. For example, the protective substance may include a cream or lotion with energy absorbing particles.

Alternatively, the waveguide may be placed in a needle and the needle inserted into the hair follicle so that the needle is in contact with the follicle lining throughout the depth of the hair follicle. The waveguide conveys energy to the needle, which in turn conducts it to the follicle lining to destroy the same.

DETAILED DESCRIPTION OF THE INVENTION

The present invention involves the insertion into a hair follicle of an invasive element through which laser energy is emitted. The invasive element may be a waveguide with a frosted tip that contains roughened fiber along a predetermined length of the invasive element or that is a conical frosted sapphire probe that diffuses or scatters light energy in a radial direction. Frosted tips are known conventionally, such as having the fiber properties discussed in H. Fujii et al, "Light scattering properties of a rough-ended optical fibre", Optics and Laser Technology®, February 1984, pp. 40–44. Optical waveguides with frosted tips are available commercially, such as those manufactured by ITT or mentioned in European Patent No. 292,621 (inventor: Norio Daikuzono, November, 1988), U.S. Pat. No. 4,736,743 (Norio Daikuzono, April 12, 1988) and U.S. Patent No. 5,139,495 (Norio Daikuzono, Aug. 18, 1992). The contents of this article and these patents are incorporated herein by reference. The waveguide may also have a diamond tip that diffuses or scatters light outwardly, particularly when used with a $CO_2$ laser.

The pulsed optical source may be a laser. The pulsed energy is directed to kill cells that cause hair growth. The blood vessels of the papilla and the entire lining of the follicle including the hair shaft, the hair bulge and hair bulb, are destroyed. This assures permanent or long term hair removal. The light source or laser is a pulsed optical source of energy between 50mJ and 1000mJ, preferably 100 –300mJ. The pulse duration of the laser source is preferably between 100 microseconds and 3 milliseconds to ensure a controlled coagulation depth of approximately 100 –300 microns. However, up to 10 milliseconds in pulse duration is feasible. The preferred embodiment uses a holmium 2.1 $\mu$ wavelength laser, although other pulsed lasers including Nd:YAG, ruby or $CO_2$ can be used.

The calculated energy necessary for laser hair depilation with a fiber is as follows for a typical hair follicle 0.2 mm. long, 0.2 mm. wide and 6 mm. long. It is desirable to elevate temperature to about 100 °C.(or at least to 600 C.). In this example, therefore:

Volume: $0.2 \times 0.2 \times 6 mm^3 = 0.24 \times 10^{-3}$ cm$^3$

Temperature: $\Delta T = 100° C. - 40° C. = 60°$ C.

Heat Capacity: $C = 4.2 J/cm^3$

Necessary Energy: $E = 4.2 \times 0.24 \times 10^{-3} \times 60 = 60$ mJoul

In this example the necessary energy is 60 mjoul. In view of the size variations of hair follicle diameters and depths, necessary energy should vary between 20mJ and 400mJ per pulse. The thermal relaxation time for 1 mm thickness of tissue is known to be approximately 0.3 sec. As a result, damaging 0.1–0.2 mm depth of tissue requires a pulse duration of 3–30 msec. or less.

Figure 1:
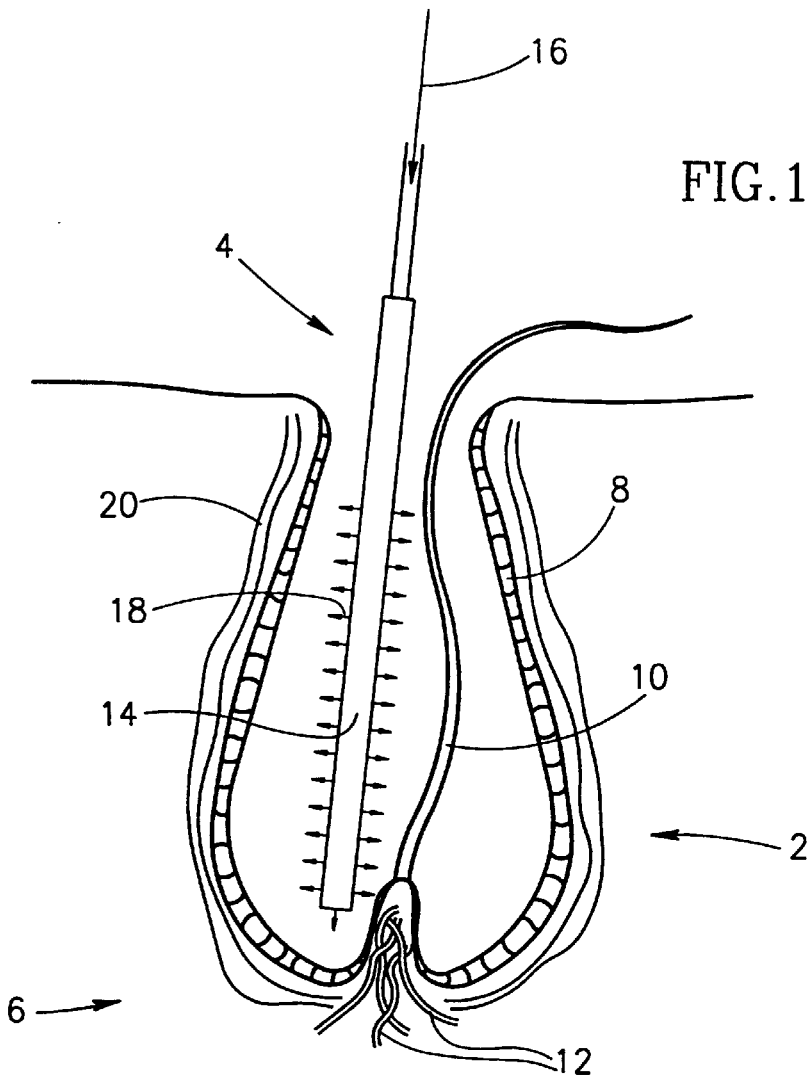
FIG. 1 illustrates in cross-section a follicle having a frosted waveguide therein radially dispersing laser energy.

FIG. 1 illustrates in cross-section a hair follicle 2 having an elongated waveguide 4 therein that radially disperses laser energy along a predetermined length. Preferably, the waveguide 4 has a frosted tip 14 that extends from the distal end by this predetermined length. The frosted tip is elongated with an axis extending in a direction of this elongation that allows the laser energy to disperse from the frosted tip in a radial direction relative to the axis and in a substantially uniform manner.

Papilla or bulb cells 6 are shown at the bottom portion of the follicle. Bulge cells 8 are further towards the surface of the skin. Hair shaft 10 is nourished by capillaries 12. Pulsed laser energy is provided from a source (not shown) to the waveguide 4 in the direction of arrow 16. Laser radiation then radiates radially from frosted tip 14 as indicated by arrows 18, thereby destroying the blood vessels of the capillaries 12 and the entire lining of the follicle including the hair shaft 10, the hair bulge 8 and hair bulb 6. Outlying skin is not damaged since laser energy does not penetrate beyond follicle lining 20.

The diameter of the fiber of the waveguide is about 0.3 mm. The length of the frosted portion of the fiber from its distal end is approximately 2 mm. The lasers which may be used include a holmium laser in the green wavelength, a pulsed dye laser in the green wavelength, a frequency doubled Nd:YAG laser at 1.44 microns, an erbium laser at 3.0 microns and a $CO_2$ laser at 10.6 microns. The preferred laser for this embodiment is a holmium laser at a wavelength of 2.1 microns.

The laser beam is more strongly absorbed by tissue immediately surrounding the frosted tip. Absorption depth is approximately 250 microns, thereby destroying the tissue lining of the hair follicle but avoiding deep penetration of the outlying skin that could otherwise lead to overheating and damage of an external surface of the skin. Pulse duration should be up to 1 millisecond, which the relaxation time of tissue for that depth. The outlying skin is not scarred or otherwise damaged since the laser energy transmitted from the waveguide does not penetrate beyond the follicle lining. General parameters for the holmium laser in accordance with the present invention are: energy per pulse: 200 mjoule; repetition rate: 10 hertz; wavelength: 2.1 micron; pulse duration: about 200 microseconds.

Figure 2:
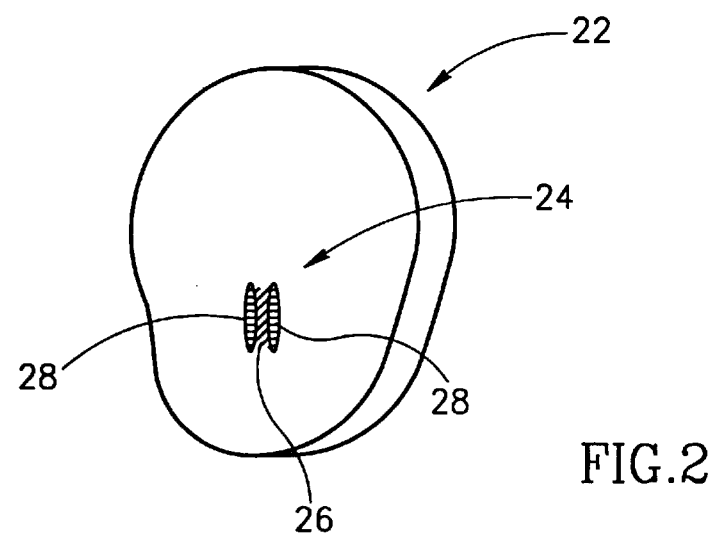
FIG. 2 illustrates a top view of one half of sliced tissue after applying laser radiation between both halves using a diffusing waveguide.

FIG. 2 shows a top view of one half of sliced tissue (e.g., a chicken leg of dead tissue) after applying laser radiation between both halves using a waveguide that is sandwiched between the two halves and in good contact with each. A typical thermal radiation pattern 24 is illustrated in which may be seen the location 26 of thermal damage to the tissue where the waveguide was placed and areas 28 of coagulation from the thermal damage.

To generate this pattern 24, the laser was turned on for a short time duration of about 200 usec. per pulse. The other half of the sliced tissue was then removed so as to visualize the resulting thermal imprint and measure the extent of thermal damage. This test was performed using from 1 pulse to 10 pulses.

The results indicate that one pulse does not cause visible damage. Two pulses provide visible damage of 300 microns in each direction surrounding the fiber, as shown in areas of coagulation 28. The length of the damaged zone is 2.5 mm. Thermal necrosis depth for 5 pulses is close to 500 microns, which is likely too large. These in vitro results suggest an optimal energy level of 200– 400mJ.

In a single clinical application, the 2 mm holmium fiber tip was inserted into a follicle of a thumb, after removing the original hair with a forcep. Four pulses were fired from the holmium laser. After a brief (4 hours) red inflammative period, the coagulated follicle reduced to a 1.5 mm spot with some erythema. Two to four pulses of a holmium beam are considered optimal.

Figure 3:
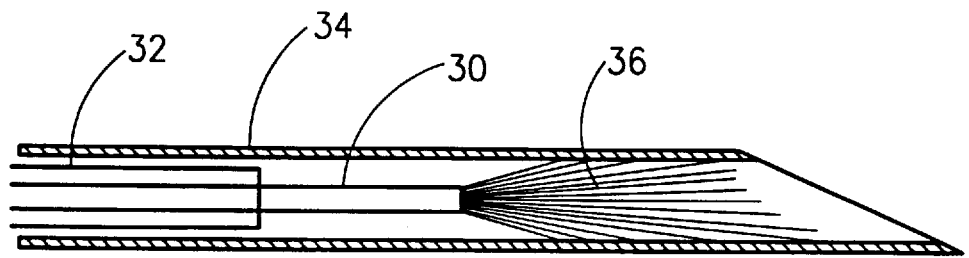
FIG. 3 illustrates a side cross-sectional view of a flat fiber in a protective sheath within a metal needle.

Turning to FIG. 3, a further embodiment is shown that employs a pulsed laser which also may operate at a wavelength which penetrates skin and a thin (200 microns) waveguide inserted into a thin metallic probe or needle. For instance, the waveguide may include a flat fiber 30 in a protective sheath 32 within a conductive metal needle 34. The waveguide inserted into the needle 34 could alternatively be a diffusing fiber such as frosted waveguide 4 shown in FIG. 1. The needle is made of an excellent heat conductive material such as metal. The needle is inserted into a hair follicle (not shown) and laser energy 36 is emitted from the fiber into the needle in order to heat the needle. The radiation emitted from the fiber is substantially absorbed by the needle wall given the proper needle aspect ratio. The hot needle transfers the heat energy to the surrounding follicle tissue in a very short time duration after one hundred microseconds, generally for 100 –3000 microseconds. Since the tip is in contact with the hair follicle walls, the hot tip will heat the walls and coagulate them. Preferably, the beam which is emitted from the fiber tip is heating the needle for a time duration equal to the laser pulse duration.

The laser or light source is usually of 200–1000mJ energy level, and pulse duration shorter than 3 milliseconds. The laser can be a Nd:YAG laser, a ruby laser or any other laser such as $CO_2$, holmium, frequency doubled Nd:YAG, a Xenon lamp or a dye laser in the yellow or other wavelength. Penetrating laser energy may be used given the use of the needle to absorb and properly transmit the energy. This embodiment of the invention is preferably performed with a Nd:YAG laser.

The method assures heating of the needle along a predetermined length. The length can be a little shorter than the entire follicle length in order to avoid coagulation of the upper portion of the follicle which is visible near the skin. The metallic needle heats up very quickly and immediately transfers heat to the surrounding tissue because of its high heat conductivity. Because the needle has very thin walls of approximately 800 microns, heat is transferred directly to tissue and not backward along the needle. The laser energy travels from the needle radially outward to all areas of the follicle which contribute to hair growth.

An in vitro experiment was performed to determine the extent of thermal necrosis resulting to the tissue surrounding the needle. A Nd:YAG laser beam was fired into the metallic probe which was inserted into tissue sliced as in the experiment previously described. As expected the thermal necrosis depth was about 350 microns. Thermal damage occurred precisely around the needle walls and not beyond. Thus one can achieve control of the temporal and geometrical parameters of heating the needle and the resultant length and depth of thermal damage.

Other means of heating the needle may be applied than the use of laser energy such as a lamp source.

Figure 4:
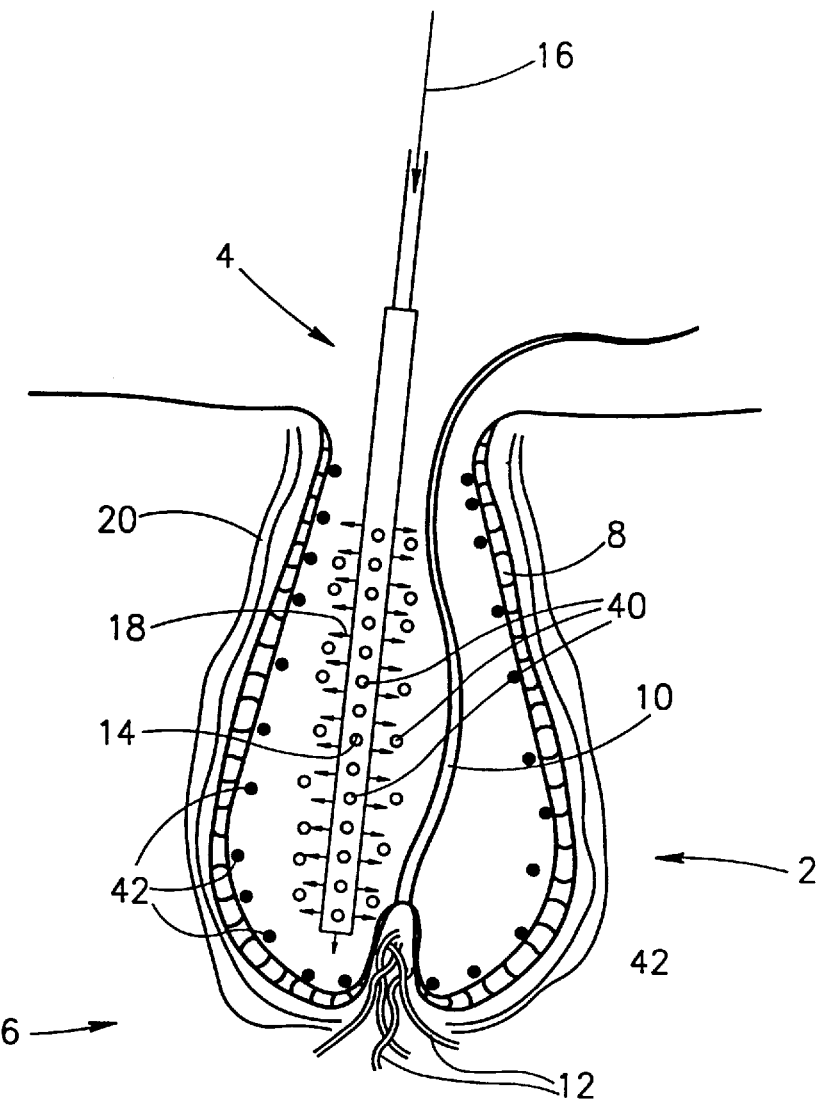
FIG. 4 illustrates in cross-section a follicle as in FIG. 1, except further showing energy absorbing particles.

FIG. 4 represents still another embodiment that utilizes a pulsed laser that generates laser radiation, which may penetrate deep into the tissue if left unchecked. A waveguide is provided of the type as described in the embodiment of FIG. 1. To counter such deep penetration, energy absorbing particles are first embedded into the follicle. These particles are provided in a particle dispersant such as a lotion, which is preferably oil based, or an oil.

The laser may be a frequency doubled Nd:YAG laser preferably at 1.06 microns, ruby laser preferably at 0.64 microns, a xenon light source, a dye laser in the yellow or other wavelength, and an alexandrite laser. A frequency doubled Nd:YAG laser is preferred. Any wavelength can be used. The laser may also be a holmium, $CO_2$, frequency doubled Nd:YAG or a dye laser in the yellow or other wavelength, although the energy-absorbing lotion is not necessary with these lasers. Laser energy level is usually 100mJ –1000mJ and time duration shorter than 3 milliseconds.

The same type of waveguide used with the holmium laser is used here, e.g., a frosted fiber. With penetrating laser energy such as that provided doubled Nd:YAG laser, it is preferable to also insert into the follicles energy absorbing particles. The energy absorbing particles may each be about 10 micrometers in size.

Indeed, black particles 42 and white particles 40 may both be used as shown schematically in FIG. 4, such as by first introducing into the hair follicle the oil containing the black particles to fill it, dipping the optical fiber in oil containing white particles, and inserting the optical fiber (with the white particle layer) into the hair follicle that is filled with the black particle oil. The white particles may be diamond, sapphire, quartz or the like to scatter the laser radiation by reflection to contain the laser radiation within the hair follicle. The black particles may be carbon black or the like to absorb the remaining reflected radiation. Both help ensure protection of the skin outlying the follicle lining against damage from overheating. Of course, either black or white particles alone may be used. U.S. Pat. No. 4,139,495, for instance, discusses the use of such scattering particles and absorbing particles and all the different varieties mentioned therein are equally applicable here. The contents of U.S. Pat. No. 5,190,535, (Norio Daikuzono, Mar. 2,1993) is incorporated herein by reference and the types of scattering particles and absorbing particles described therein are equally applicable here.

The black particles may be embedded into the hair follicle adjacent the lining to absorb radiation and then heat up to transfer heat to the lining of the follicle sufficient to coagulate the lining because they are embedded. By absorbing the laser radiation, the particles also protect the outlying skin by blocking the laser radiation from effecting deep penetration into surrounding tissue.

The white particles primarily reflect the laser radiation. Because of the prevalence of reflection, multiple reflections cause the laser radiation to scatter and be retained within the follicle and block them from penetrating deep into the outlying skin. Therefore white reflecting particles may be embedded into the hair follicle adjacent the lining and perform just as effectively as black absorbing particles.

The present invention provides a method of destroying a follicle directly while preventing damage to the skin outside the follicle lining from the effects of radiation such as overheating. By targeting all cells of a follicle which contribute to new hair growth, the method of the present invention as claimed strives for permanent or long term results.

The light radiation source that generates radiation through the optical waveguide may be a ruby laser, an alexandrite laser, a dye laser, a pulsed Nd:YAG laser or a xenon light source where the energy absorbing particles are applied as a protective layer to protect the outlying skin (including its external surface) against overheating due to the otherwise deep penetration of the radiation. The source may also be a holmium, $CO_2$, or frequency doubled Nd:YAG laser, but the protective layer of energy absorbing particles is not necessary in conjunction with these types of lasers because their radiation will not penetrate into tissue sufficient to damage the outlying skin or external layer of the skin.

What is claimed is:

1. A method to remove hair, comprising the steps of:
   inserting an invasive element into a hair follicle, said invasive element being elongated and having an axis in a direction of elongation of the invasive element; and
   applying laser energy into said invasive element, said invasive element including a frosted tip having roughened fiber that scatters the laser energy in a radial direction relative to said axis along an entire length of the frosted tip, the laser energy being of sufficient energy and pulse duration so as to substantially damage an entire lining of the hair follicle.

2. A method as in claim 1, wherein said step of applying includes pulsing the laser energy so that each pulse has an energy level of between 20 millijoules and 400 millijoules inclusive and a pulse duration of at most 30 milliseconds.

3. A method as in claim 1, further comprising the step of embedding energy absorbing particles into the hair follicle before the step of applying, said particles absorbing the diffused laser energy.

4. A method as in claim 3, wherein the step of embedding includes introducing a lotion into the hair follicle, said lotion containing said energy absorbing particles.

5. A method as in claim 3, wherein said energy absorbing particles are black that absorb the diffused laser energy sufficient to protect the outlying skin from an extent of penetration of the laser energy otherwise available.

6. A method as in claim 3, wherein said energy absorbing particles are white reflecting particles that yield multiple reflections of the diffused laser energy.

7. A method as in claim 3, wherein said energy absorbing particles are a mixture of black absorbing particles and white reflecting particles.

8. A method as in claim 3, wherein said step of applying includes pulsing the laser energy so that each pulse has an energy level of between 20 millijoules and 1000 millijoules inclusive and a pulse duration shorter than 30 milliseconds.

9. A method as in claim 1, wherein the step of inserting includes inserting a conductive needle into the hair follicle, the needle having a chamber in which is inserted the frosted tip portion.

10. A method as in claim 9, wherein the step of applying pulses the laser energy so that each pulse has an energy level of between 20 millijoules and 1000 millijoules inclusive and a pulse duration less than 30 milliseconds.

11. An apparatus to remove hair, comprising:
    an invasive element that is elongated and has an axis in a direction of elongation of said invasive element;
    a laser that applies laser energy into said invasive element, said invasive element including a frosted tip that scatters the laser energy in a radial direction relative to said axis along an entire length of the frosted tip, the laser providing a sufficient amount of the laser energy and pulse duration so as to substantially damage an entire lining of the hair follicle; and
    a conductive needle having a chamber; said frosted tip portion being slidably inserted in said chamber.

12. An apparatus as in claim 11, wherein said laser pulses the laser energy so that each pulse has an energy level of between 20 millijoules and 400 millijoules inclusive and a pulse duration of at most 30 milliseconds.

13. An apparatus as in claim 11, further comprising means for arranging energy absorbing particles to absorb the diffused laser energy that would otherwise penetrate the outlying skin.

14. An apparatus as in claim 13, wherein said energy absorbing particles are black that absorb the diffused laser energy sufficient to protect the outlying skin from an extent of penetration of the laser energy otherwise available.

15. An apparatus as in claim 13, wherein said energy absorbing particles are white that provide multiple reflections of the diffused laser energy.

16. An apparatus as in claim 13, wherein said energy absorbing particles are a mixture of black absorbing particles and white reflecting particles.

17. An apparatus as in claim 11, wherein said laser pulses the laser energy so that each pulse has an energy level of between 20 millijoules and 1000 millijoules and a pulse duration shorter than 30 milliseconds.

* * * * *